(12) United States Patent
Gilkey et al.

(10) Patent No.: US 11,707,296 B2
(45) Date of Patent: *Jul. 25, 2023

(54) SEALING DEVICES AND SURGICAL IMPLEMENTS COMPRISING SAME

(71) Applicant: ClearCam Inc., Austin, TX (US)

(72) Inventors: James Landon Gilkey, Dripping Springs, TX (US); Christopher Robert Idelson, Austin, TX (US)

(73) Assignee: ClearCam, Inc., Austin, TX (US)

( * ) Notice: Subject to any disclaimer, the term of this patent is extended or adjusted under 35 U.S.C. 154(b) by 431 days.

This patent is subject to a terminal disclaimer.

(21) Appl. No.: 17/092,652

(22) Filed: Nov. 9, 2020

(65) Prior Publication Data

US 2022/0142669 A1 May 12, 2022

(51) Int. Cl.
*A61B 17/34* (2006.01)
*A61M 13/00* (2006.01)
*A61B 17/00* (2006.01)

(52) U.S. Cl.
CPC ....... *A61B 17/3423* (2013.01); *A61M 13/003* (2013.01); *A61B 2017/00862* (2013.01); *A61B 2017/3419* (2013.01)

(58) Field of Classification Search
CPC ...... A61B 17/3423; A61B 2017/00862; A61B 2017/3419; A61B 2017/00477; A61B 17/3421; A61B 17/3462; A61M 13/003

See application file for complete search history.

(56) References Cited

U.S. PATENT DOCUMENTS

| | | | |
|---|---|---|---|
| 4,726,374 A | * | 2/1988 | Bales ................ A61M 39/0613 606/108 |
| 6,439,541 B1 | | 8/2002 | Nosel et al. |

(Continued)

FOREIGN PATENT DOCUMENTS

EP 2042114 B1 7/2011

OTHER PUBLICATIONS

John M. Uecker et al., Stop the leak!: Mitigating potential exposure of aerosolized COVID-19 during laparoscopic surgery, Surgical Endoscopy, Sep. 24, 2020, pp. 1-7, https://doi.org/10.1007/s00464-020-08006-4, Springer Science+Business Media LLC, published on-line, printed on Nov. 10, 2020.

(Continued)

*Primary Examiner* — Theodore J Stigell
(74) *Attorney, Agent, or Firm* — IVC Patent Agency; David O. Simmons (57) ABSTRACT

Disclosed herein are sealing devices configured for improving sealing functionality with an engaged extension member of an apparatus. More specifically, disclosed herein are trocar sealing devices configured for improving insufflation gas containment in relation to trocars (and/or other related type of devices) that are used for enabling a surgical instrument such, for example, a laparoscope, to gain access to an abdominal cavity (or other body cavity). By providing for such improved insufflation gas containment, sealing devices as disclosed herein are particularly advantageous, desirable and useful in view of long-standing reasons for limiting insufflation gas leakage and in view of newly recognized reasons stemming from outbreak of COVID-19 disease for limiting insufflation gas leakage.

20 Claims, 7 Drawing Sheets

(56) References Cited

U.S. PATENT DOCUMENTS

| | | |
|---|---|---|
| 11,045,220 B1* | 6/2021 | Gilkey .............. A61B 17/3423 |
| 2004/0138676 A1 | 7/2004 | Crabtree |
| 2007/0255219 A1* | 11/2007 | Vaugh .............. A61B 17/3423 |
| | | 604/167.02 |
| 2008/0125716 A1 | 5/2008 | Cruz |
| 2010/0193516 A1 | 8/2010 | LaBean et al. |
| 2017/0360476 A1 | 12/2017 | Pantalos |

OTHER PUBLICATIONS

Stefano Angioni, Laparoscopy in the coronavirus disease 2019 (COVID-19) era, Gynecological Surgery, May 14, 2020, pp. 1-4, https://doi.org/10.1186/s10397-020-01070-7, Springer Nature, published on-line, printed on Nov. 10, 2020.

Tushar Pawar et al., The Technique and Justification for Minimally Invasive Surgery in COVID-19 Pandemic: Laparoscopic Anterior Resection for Near Obstructed Rectal Carcinoma, Journal of Laparoendoscopic & Advanced Surgical Techniques, 2020, pp. 485-487, DOI: 10.1089/lap.2020.0241, vol. 30, No. 5, Mary Ann Liebert, Inc.

Resources for Smoke & Gas Evacuation During Open, Laparoscopic, and Endoscopic Procedures, Society of American Gastrointestinal and Endoscopic Surgeons, Mar. 29, 2020, pp. 1-5, https://www.sages.org/resources-smoke-gas-evacuation-during-open-laparoscopic-endoscopic-procedures/, published on-line, printed on Nov. 10, 2020.

Mark Soliman, Controversies in CO2 Insufflation and COVID-19, Techniques in Coloproctology, May 20, 2020, pp. 1-4, https://doi.org/10.1007/s10151-020-02237-2, Springer Nature, published on-line, printed on Nov. 10, 2020.

* cited by examiner

FIG. 5 and surgical implements comprising same

SEALING DEVICES AND SURGICAL IMPLEMENTS COMPRISING SAME

FIELD OF THE DISCLOSURE

The disclosures made herein relate generally to sealing devices and, more particularly, to sealing devices for use with apparatuses such as, for example, surgical instruments used during manual and robotic surgical procedures that have an extension portion that is engaged with a sealing device.

BACKGROUND

Surgical procedures utilizing in vivo visualization of target surgical sites are well known as a form of a concealed operation site. Examples of these surgeries include, but are not limited to, endoscopic surgery, laparoscopic surgery, thoracoscopic surgery and the like. These surgical procedures all utilize a surgical instrument having an integrated visualization device for providing in vivo visualization of a target surgical site within a surgical space of the patient. Although it is common for the surgical instrument to be referred to in the context of the specific type of surgical procedure (e.g., endoscope for endoscopic surgery, laparoscope for laparoscopic surgery, and the like), these surgical instruments are generally referred to herein as an "endoscope".

Figure 1:
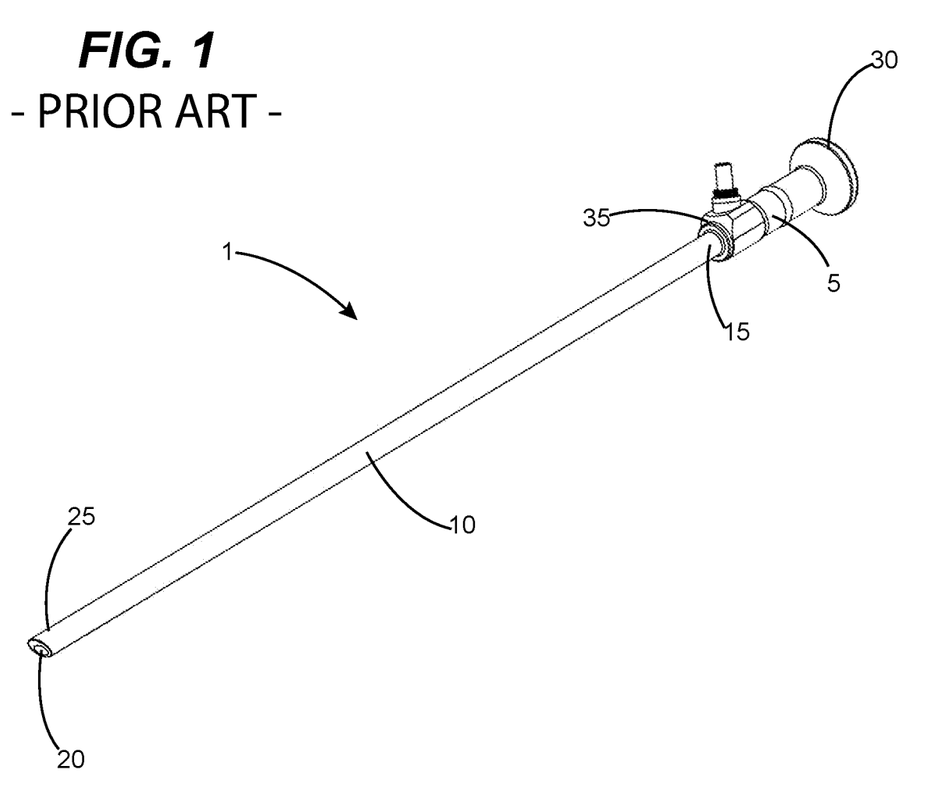
FIG. 1 is a perspective view showing a prior art endoscope.

As shown in FIG. 1, an endoscope 1 used in these surgical procedures is characterized as having a user interface portion 5 and an extension member 10 connected at its proximate end 15 to the user interface portion 5. Scopes for endoscopic surgery generally have an extension member that is substantially flexible, whereas scopes for other types of surgical procedures—e.g., for laparoscopic surgery, as shown in FIG. 1—generally have an extension member 10 that is substantially rigid. The extension member 10 has an imaging element 20 such as a lens at its distal end portion 25. The imaging element 20 can have an exposed surface that is typically generally flush with or that defines an end face of the extension member 10. The imaging element 20 is connected to an optical fiber or other image transmitting element that is internal to the endoscope. The optical fiber or other image transmitting element extends along the length of the extension member 10 and terminates at an eyepiece 30 on the user interface portion 5. The eyepiece 30 enables the imaging element 30 to be connected to a visualization device (e.g., a camera connected to a visual display console) through which target surgical sites can be viewed by surgery personnel.

Figure 2:
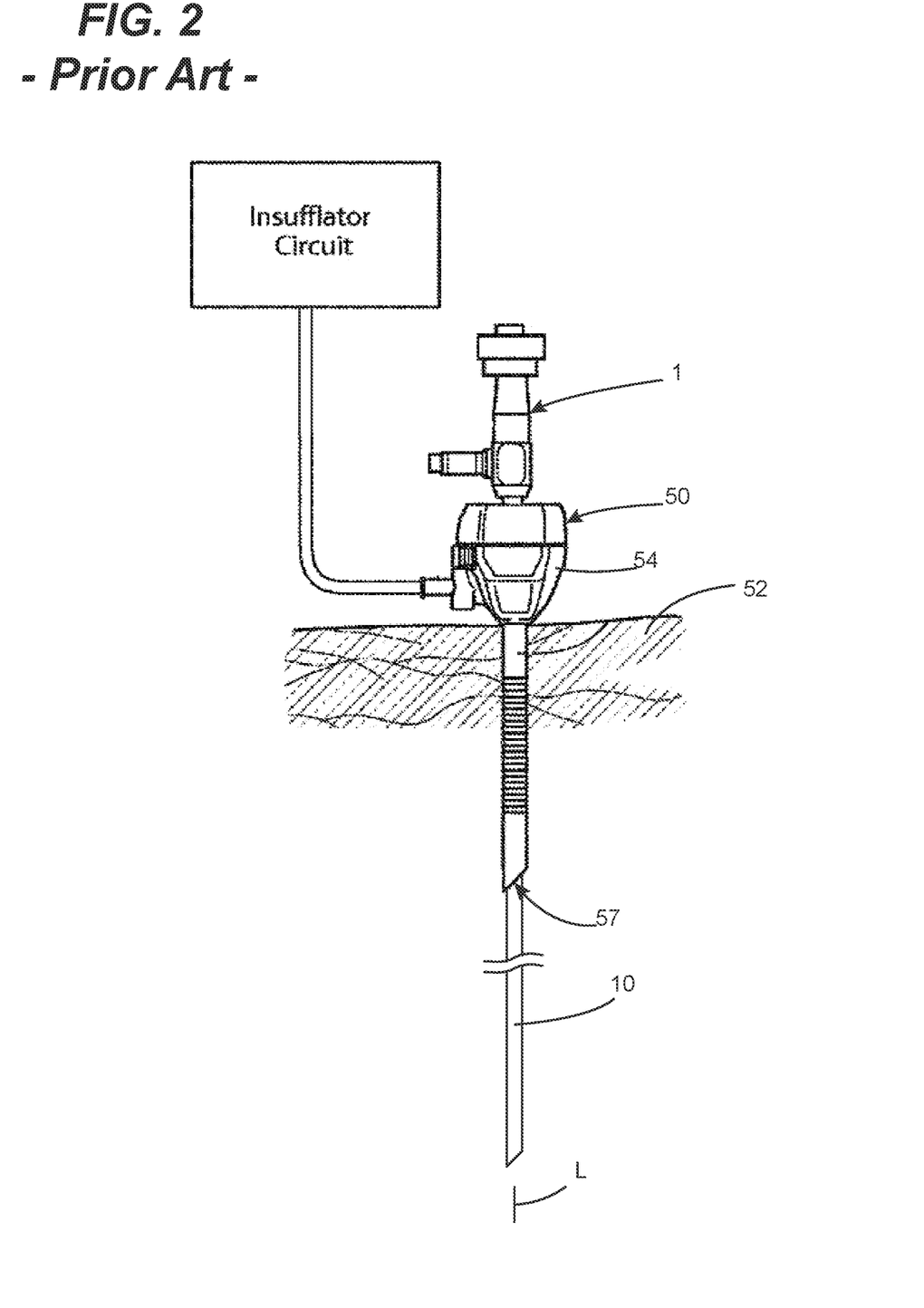
FIG. 2 is a diagrammatic view showing a prior art trocar with the prior art endoscope of FIG. 1 engaged therewith.

As shown in FIG. 2, during a surgical procedure, the endoscope 1 (i.e., a surgical instrument) is operably engaged with a trocar 50 (i.e., an example of a surgical implement). As is well known in the art, trocars such as the trocar 50 serve as an access device for placing a surgical instrument through an abdominal wall 52 of a patient. The trocar 50 has a seal housing 54 and a cannula 56 attached to the seal housing 54. A central passage 57 of the trocar 50 (i.e., the working channel) extends through the seal housing 54 and the cannula 56, thereby defining a working channel extending through the trocar 50 along a longitudinal axis L of the trocar 50. The central passage 57 has an inside diameter sized as a function of an outside diameter of an extension member of a surgical instrument intended to be used with the trocar 50 (e.g., extension member 10 of the endoscope 1). The cannula 56 is adapted for being placed through the abdominal wall 52 of the patient. Once the trocar 50 is placed, the extension member of the endoscope 1 (or other type of surgical instrument) is placed through the working channel of the trocar 50 for enabling abdominal cavity access for a distal end of the endoscope 1. The seal housing 54 includes one or more seals for providing the functionalities of limiting leakage of insufflation gas when the surgical instrument is within the working channel of the trocar 50 and, limiting leakage of insufflation gas when the surgical instrument is withdrawn from within the working channel of the trocar 50. Conventional seals integral to trocars are well known in the art.

It is also well known in the art that a surgical instrument such as, for example, the endoscope 1 is moved in a plurality of movement directions during a surgical procedure while engaged with a trocar. For example, as shown in FIG. 2, the endoscope 1 is well known to be moved in an axial direction along a longitudinal axis L of the trocar 50 (i.e., axial movement), to be moved in a pivotal manner about one or more pivot axes extending perpendicular to the longitudinal axis L of the trocar 50 (i.e., pivotal movement) and to be moved rotationally about the longitudinal axis L of the trocar 50 (i.e., rotational movement). Additionally, the longitudinal axis of the endoscope 1 can be laterally offset of the longitudinal axis L of the trocar 50 (i.e., not colinear axes). The one or more seals of the trocar 50 are intended to provide sufficient mitigation of insufflation gas leakage during such types of movement of the surgical instrument. Conventional trocars are known to exhibit insufflation gas leakage during both static positioning and dynamic movement of a surgical instrument engaged with a trocar.

Limiting insufflation gas leakage at the interface of a trocar and surgical instrument is desirable for several long-standing reasons. One such long-standing reason is maintaining necessary insufflation of a patient's abdominal cavity. Another such long-standing reason is reducing cost of insufflation gas utilized during a surgical procedure. Still another such long-standing reason is reducing gas-carried particles from compromising sealing functionality provided by the one or more seals of the trocar.

Notably, the recent emergence of coronavirus disease COVID-19 presents a new and potentially crucial reason for limiting insufflation gas leakage at the interface of a trocar and surgical instrument. Prior to its leakage, insufflation gas resides within the abdominal cavity. As such, for a patient who is positive for COVID-19, the insufflation gas may become contaminated from exposure to particulate matter (e.g., solid, liquid and/or gaseous materials) within the patient's abdominal cavity. Accordingly, the potential exists for leaked insufflation gas to expose medical personnel within an operating room to coronavirus and to contaminate the operating room with coronavirus. For apparent reasons, both of these potential situations are highly undesirable. Thus, particularly in view of the emergence of COVID-19, it is desirable to further limit, if not inhibit, the levels of insufflation gas leakage present at the interface of a trocar and surgical instrument during a surgical procedure when a conventional trocar is used for providing abdominal cavity access.

Therefore, an effective, efficient and reliable approach for improving insufflation gas containment within a trocar would be advantageous, desirable and useful.

SUMMARY OF THE DISCLOSURE

Embodiments of the present disclosure are directed to improving insufflation gas containment during a surgical procedure when a trocar is used for providing abdominal cavity access. More specifically, embodiments of the present disclosure are directed to improving insufflation gas containment in relation to trocars (and/or other related type of devices) that are used for enabling a surgical instrument such, for example, a laparoscope, to gain access to an abdominal cavity (or other body cavity). By providing for such improved insufflation gas containment, embodiments of the present disclosure are advantageous, desirable and useful in view of long-standing reasons for limiting insufflation gas leakage and in view of newly recognized reasons stemming from outbreak of COVID-19 disease for limiting insufflation gas leakage.

In one or more embodiments of the present disclosure, a sealing device for a trocar configured for use with a surgical instrument comprises an extension member seal and a securement body attached to the extension member seal. The extension member seal has a central passage with a diameter enabling an extension member of the surgical instrument to be sealingly engaged therewith. The securement body includes an elongated skirt in a rolled configuration and wherein the elongated skirt is adapted for being unrolled into secure engagement with one or more side surfaces of a seal housing of the trocar.

In one or more embodiments of the present disclosure, a sealing device for a trocar configured for use with a surgical instrument comprises an extension member seal and a securement body attached to the extension member seal. The extension member seal comprises a sealing member, a compressive force material and a retention body. The opposing end portions of the sealing member are each retained by a respective one of spaced-apart sealing member retention portions of the retention body whereby an interior space is provided between the sealing member and the retention body and wherein the compressive force material extends around the sealing member in contact therewith within the interior space. The securement body includes one or more engagement portions adapted for being selectively engageable with a seal housing of the trocar.

In one or more embodiments of the present disclosure, a trocar comprises a trocar body and extension member seal mounted within the central passage of the seal housing. The trocar body comprising a seal housing and a cannula attached to the seal housing, wherein a longitudinal axis of a central passage of the seal housing is colinearly with a longitudinal axis of a central passage of the cannula. The extension member seal comprises a sealing member, a compressive force member and a retention body. The opposing end portions of the sealing member are each retained by a respective one of the spaced-apart sealing member retention portions of the retention body whereby an interior space is provided between the sealing member and the retention body. The compressive force member extends around the sealing member in contact therewith within the interior space.

In one or more embodiments of the present disclosure, a method of reducing insufflation gas leakage from a trocar comprising a plurality of steps. A step is performed for providing a trocar comprising a seal housing and a cannula attached to the seal housing. The trocar has a working channel jointly defined by a central passage of the seal housing and a central passage of the cannula. A longitudinal axis of the central passage of the seal housing extends colinearly with a longitudinal axis of the central passage of the cannula thereby jointly defining a longitudinal axis of the working channel. A step is performed for providing a sealing device comprising an extension member seal and a securement body attached to the extension member seal. One or more seal housing engagement portions of the securement body are selectively engageable with the seal housing. A step is performed for contacting the sealing device with a top surface of the seal housing. Thereafter or in conjunction with contacting the sealing device with a top surface of the seal housing, a step is performed for engaging said one or more seal housing engagement portions of the securement body with the seal housing.

It is an object of one or more embodiments of the present disclosure for the elongated skirt to extend entirely around the extension member seal and the elongated skirt to be concentric with the central passage of the extension member seal.

It is an object of one or more embodiments of the present disclosure for the elongated skirt to be a sleeve and the sleeve is attached at an end portion thereof to the extension member seal.

It is an object of one or more embodiments of the present disclosure for the elongated skirt being adapted for being unrolled including the elongated skirt being made from a conformable, elastic material.

It is an object of one or more embodiments of the present disclosure for the elongated skirt, the sealing member, or both to be made from one of a material comprising silicone and a material consisting essentially of silicone.

It is an object of one or more embodiments of the present disclosure for a support body to be attached to the extension member seal, for the support body to include a central passage through which the central passage of the extension member seal is accessible, for the support body to be attached to an upper portion of the extension member seal and for the elongated skirt to be positioned adjacent to a lower portion of the extension member seal.

It is an object of one or more embodiments of the present disclosure for the compressive force member to be a ring-shaped member.

It is an object of one or more embodiments of the present disclosure for the ring-shaped member to be a helically-wound spring having at least one of opposing end portions thereof overlapping and opposing end portions thereof attached thereto.

It is an object of one or more embodiments of the present disclosure for the ring-shaped member to be an O-ring.

It is an object of one or more embodiments of the present disclosure for the sealing member to be a sleeve having opposing end portions thereof engaged with the spaced-apart sealing member retention portions of the retention body.

It is an object of one or more embodiments of the present disclosure for engagement of the compressive force member with the sealing member to cause the compressive force member to be in a radially-expanded state such that a compressive force is exerted on the sealing member by the compressive force member.

It is an object of one or more embodiments of the present disclosure for the compressive force material to be engaged with the sealing member such that the compressive force material is a radially-expanded state to cause a compressive force is exerted on the sealing member by the compressive force material.

It is an object of one or more embodiments of the present disclosure for the compressive force material to comprise one of a ring-shaped piece of material and a c-shaped piece of material.

It is an object of one or more embodiments of the present disclosure for the compressive force material to comprise a helically-wound spring having at least one of opposing end portions thereof overlapping and opposing end portions thereof attached thereto.

It is an object of one or more embodiments of the present disclosure for the compressive force material to comprise a fluidic material.

It is an object of one or more embodiments of the present disclosure for the fluidic material to at least partially fill the interior space between the sealing member and the retention body.

It is an object of one or more embodiments of the present disclosure for a method to include the step of aligning a longitudinal axis of a central passage of the extension member seal with the longitudinal axis of the working channel prior to or in conjunction with contacting the sealing member with the sealing housing.

It is an object of one or more embodiments of the present disclosure for the step of aligning the longitudinal axis of the central passage of the extension member seal with the longitudinal axis of the working channel in conjunction with contacting the sealing device with the top surface of the seal housing to includes inserting a distal end portion of an extension member through the central passage of the extension member seal inserting the distal end portion of the extension member into the working channel.

It is an object of one or more embodiments of the present disclosure for a method to include the step of aligning the longitudinal axis of the central passage of the extension member seal with the longitudinal axis of the working channel prior to performing contacting the sealing member with the seal housing.

It is an object of one or more embodiments of the present disclosure for a method to include the steps of placing the cannula through an abdominal wall of a patient prior to contacting the sealing member with the seal housing, inserting a distal end portion of an extension member of a laparoscope through the central passage of the extension member seal after placing the trocar and prior to engaging tone or more seal housing engagement portions of the securement body with the seal housing, and inserting the distal end portion of the extension member into the working channel after placing the trocar and prior to engaging the one or more seal housing engagement portions of the securement body with the seal housing.

It is an object of one or more embodiments of the present disclosure for the one or more seal housing engagement portions of the securement body to comprise an elongated skirt in a rolled configuration, for the elongated skirt to be adapted for being unrolled into secure engagement with one or more side surfaces of the seal housing and for engaging the one or more seal housing engagement portions of the securement body with the seal housing to comprise unrolling the elongated skirt.

These and other objects, embodiments, advantages and/or distinctions of the present disclosure will become readily apparent upon further review of the following specification, associated drawings and appended claims.

DETAILED DESCRIPTION

Figure 3A:
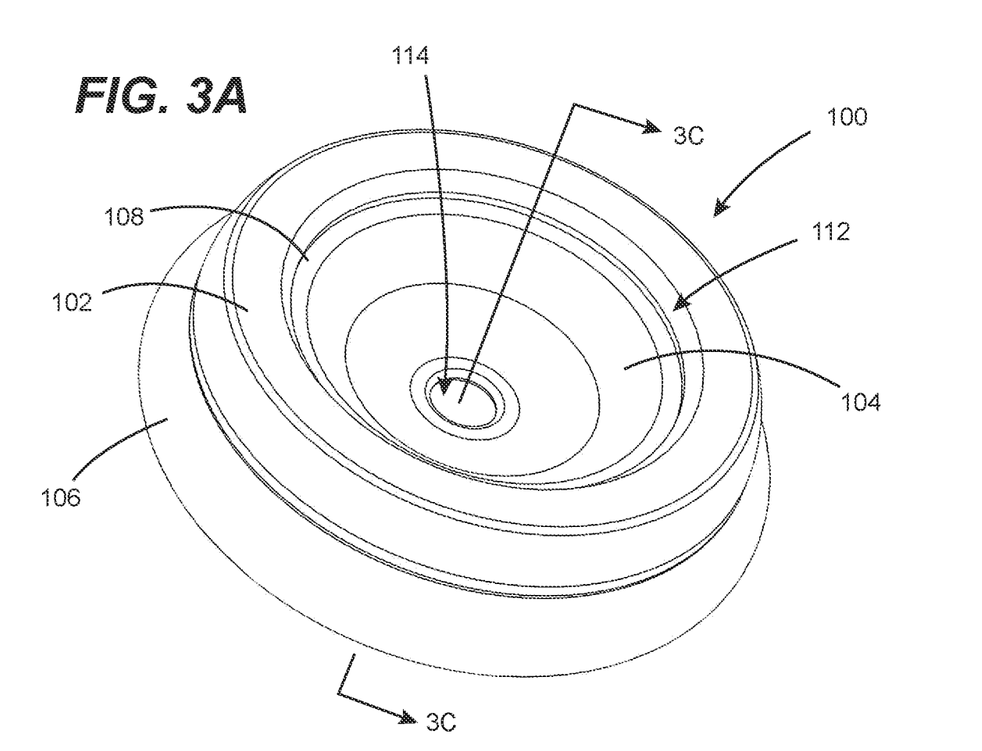
FIG. 3A is top perspective view showing a first embodiment of a trocar sealing device in accordance with the disclosures made herein.
Figure 3B:
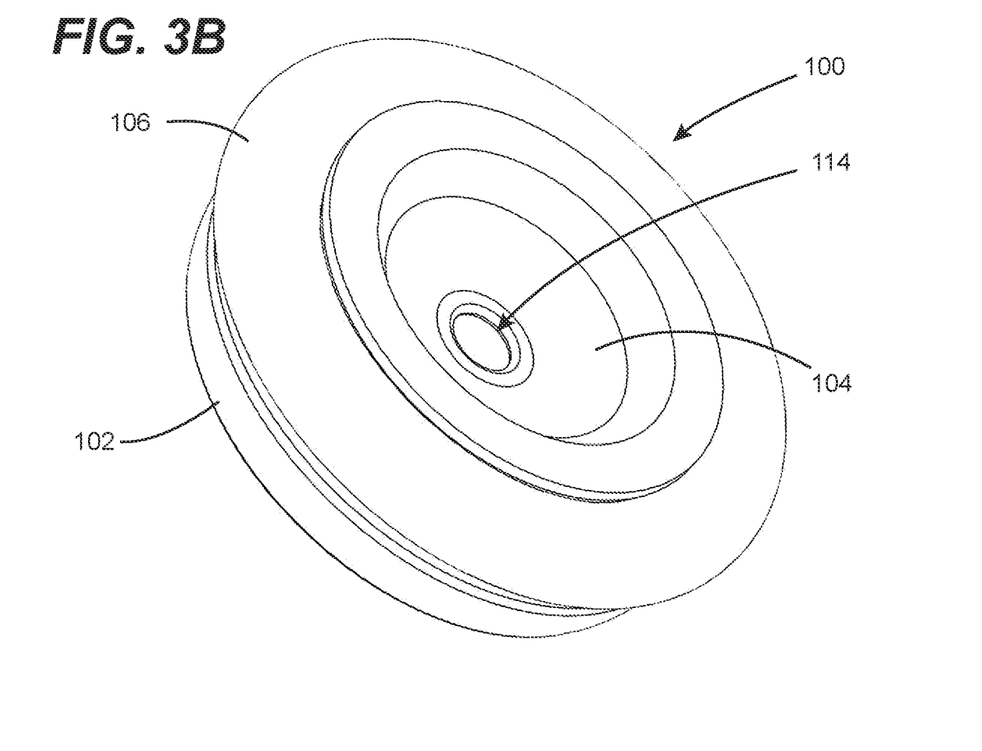
FIG. 3B is bottom perspective view of the trocar sealing device shown in FIG. 3A.
Figure 3C:
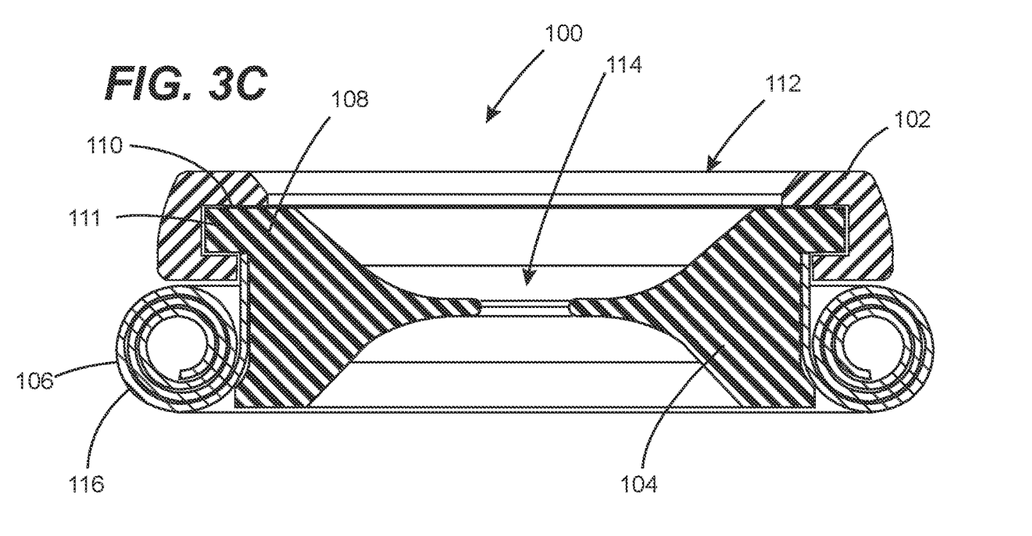
FIG. 3C is a cross-sectional view taken along the line 3C-3C in FIG. 3A.
Figure 3D:
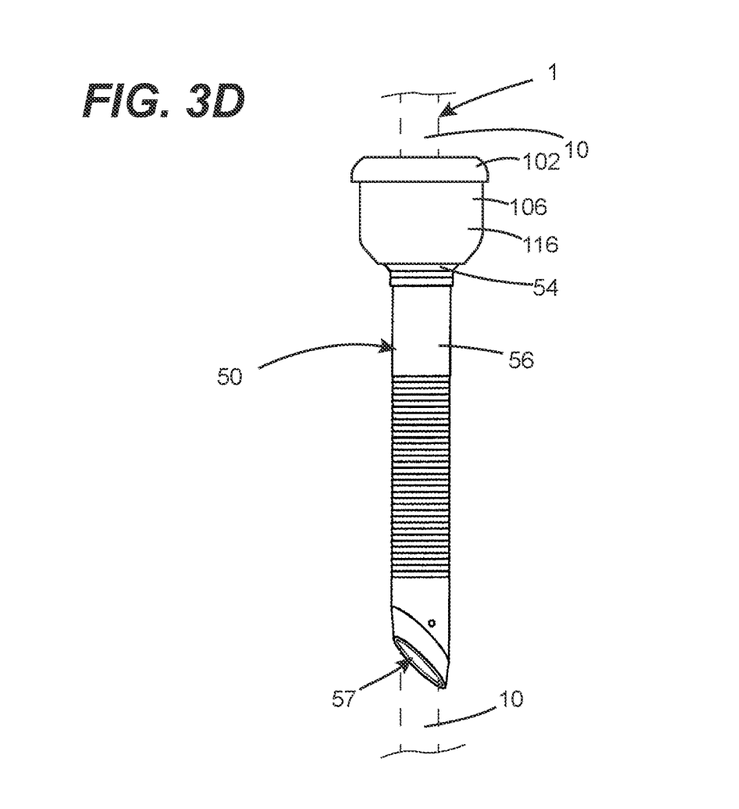
FIG. 3D is a diagrammatic view showing the prior art trocar of FIG. 2 with the trocar sealing device of FIGS. 3A-3C installed thereon.

Referring to FIGS. 3A-3D, a first embodiment of a trocar sealing device (sealing device 100) in accordance with the disclosures made herein is shown. The sealing device 100 includes a support body 102, an extension member seal 104 and a securement body 106. Jointly, as shown in FIG. 3D and discussed below in greater detail, the support body 102, the extension member seal 104 and the securement body 106 enable the sealing device 100 to be mounted on a seal housing of a trocar (e.g., the seal housing 54 of the trocar 50 of FIG. 2). Advantageously, the sealing device 100 has a structural configuration allowing it to be mounted on the a trocar and to impart the trocar with supplemental sealing functionality that serves to improve insufflation gas containment when an extension member of a surgical instrument (e.g., the endoscope 1 discussed above in reference to FIG. 1) is movably engaged with the trocar during a surgical procedure.

The support body 102 is engaged with an upper end portion 108 of the extension member seal 104. As shown in FIG. 3C, the extension member seal 104 has a groove 110 (i.e., an engagement feature) that is engaged with a flange member 111 (i.e., a mating engagement feature) of the extension member seal 104. The support body 102 has a central passage 112 through which a central passage 114 of the extension member seal 104 is accessibly. The support body 102 provides a rigid or semi-rigid structural element to engage (e.g., grasp by fingers or a hand) during installation of the sealing device 100 on a trocar. The support body 102 is preferably round but can have an overall shape other than round and can include contoured portions for enhancing finger engagement. The support body 102 can be made from a rigid or semi-rigid material (e.g., a polymeric material such as a thermoplastic or thermosetting material). Alternatively, the support body 102 can be made from a material exhibiting elasticity, but where a shape and/or bulk of the support body 102 provides the support body 102 with a rigid or semi-rigid configuration. The extension member seal 104 can be made from a resilient material—e.g., a latex material, an elastomeric material, a synthetic rubber material, or the like. In preferred embodiments, the extension member seal 104 can be made from a material comprising or consisting essentially of silicone.

The central passage 114 of the extension member seal 104 is round (or approximately round) and has an inside diameter that can be specified as a function of an outside diameter of an extension member of surgical instruments intended to be used with a trocar on which the sealing device 100 is mounted. For example, if the trocar is designed for use with surgical instruments having has an extension member with a 5 mm outside diameter, the central passage 114 of the extension member seal 104 can be dimensioned as a function of the 5*mm* outside diameter of the extension member. More specifically, the central passage 114 of the extension member seal 104 can have an inside diameter that is 0.X mm smaller than the outside diameter of the extension member, Y % smaller than the outside diameter of the extension member, or the like. The underlying objective of dimensional specification of the inside diameter of the central passage 114 of the extension member seal 104 is to form secure engagement of the material of the extension member seal 104 defining the central passage 114 around the extension member of the surgical instrument, particularly during the various modes of movement of the surgical instrument relative to the trocar—i.e., lateral. axial, pivotal and rotational movements.

The securement body 106 can be attached directly to the extension member seal 104, as shown. Alternatively, the securement body 106 can be attached to the support body 102 or to both the support body 102 and the extension member seal 104. It is disclosed herein that such attachment of the securement body 106 can be provided by one or more known attachment techniques—e.g., adhesive, thermal bonding, mechanical fixation, or the like. In one or more embodiments of the disclosures made herein, the support body 102 can be omitted.

As best shown in FIGS. 3C and 3D, the securement body 106 comprises an elongated skirt 116 (i.e., a trocar engaging member) that is provided in a rolled configuration and that can be unrolled onto the seal housing of a trocar (e.g., the seal housing 54 of the trocar 1 shown in FIG. 2). The elongated skirt 116 extends around the extension member seal 104 and is concentric with the central passage 114 of the extension member seal 104. The elongated skirt 116 preferably has a wall thickness and is made from a material having resilient and elastomeric properties enabling the elongated skirt 116 to be provided in a rolled configuration and to be unrolled into secure engagement with the seal housing of a trocar. In addition to enabling the elongated skirt 116 to be rolled and unrolled, the resilient and elastomeric properties of the material from which the elongated skirt 116 is made enables the elongated skirt 116 to exert compressive force on the seal housing of the trocar when unrolled onto it for securing the sealing device 100 in a generally fixed position on the seal housing. When the seal housing of the trocar has a non-uniform shape and/or has protrusions extending therefrom, the resilient and elastomeric properties of the material from which the elongated skirt 116 also enables the elongated skirt 116 to stretch over (i.e., be sufficiently elastic) and/or conform to such non-uniform shape and/or protrusions (i.e., be sufficiently conformable). Examples of materials exhibiting sufficient conformability and elasticity include, but are not limited to, a latex material, an elastomeric material, a synthetic rubber material, or the like. In preferred embodiments, at least the elongated skirt 116 of the securement body 106 can be made from a material comprising or consisting essentially of silicone and can be in the form of a thin-walled piece of elastic and/or conformable sleeve (e.g., a piece of tubing).

Referring to FIG. 3D, engagement of the sealing device 100 onto the seal housing of a trocar (e.g., the seal housing 54 of the trocar 50 of FIG. 2, as shown) preferably includes the central passage 114 of the extension member seal 104 to be axially aligned (e.g., precisely aligned as opposed to generally aligned) with the central passage of the trocar (e.g., the central passage 57 of the trocar 50, as shown). Such alignment serves to cause the extension member seal 104 to exert substantially uniform force onto the extension member of a surgical instrument engaged within the central passage of the trocar, thereby aiding in providing the desired secure engagement of the material of the extension member seal 104 defining the central passage 114 around the extension member of the surgical instrument, particularly during the aforementioned various modes of movement of the surgical instrument relative to the trocar.

The elongated skirt 116 of the securement body 106 is a one example of a trocar engaging element of sealing devices in accordance with the disclosures made herein. In other embodiments of one or more other sealing devices in accordance with the disclosures made herein, trocar engaging elements can have different constructions. Examples of such other constructions can include, but are not limited to, one or more engagement members (e.g., legs, protruding tabs, circumferential ring, etc.) that extend from the support body and/or extension member seal into engagement with one or more passages extending through an exterior surface of the seal housing (i.e., mating feature(s) in the form of one or more seal housing engagement portions), one or more engagement members (e.g., legs, protruding tabs, circumferential ring, etc.) that extend from the support body and/or extension member seal into engagement with one or more recess(es) within the exterior surface of the seal housing (i.e., mating feature(s) in the form of one or more seal housing engagement portions), one or more engagement members (e.g., legs, protruding tabs, circumferential ring, etc.) that extend from the support body and/or extension member seal into mechanical, adhesive and/or frictional engagement with one or more exterior surfaces of the seal housing (i.e., mating feature(s) in the form of one or more seal housing engagement portions), or the like.

Figure 4A:
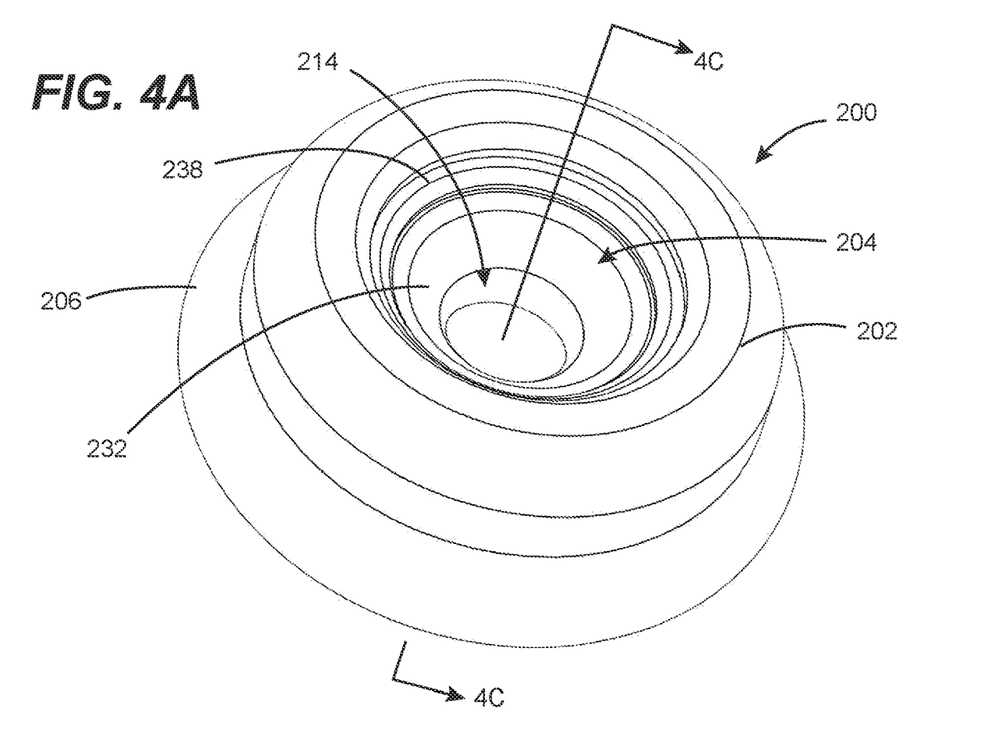
FIG. 4A is top perspective view showing a second embodiment of a trocar sealing device in accordance with the disclosures made herein.
Figure 4B:
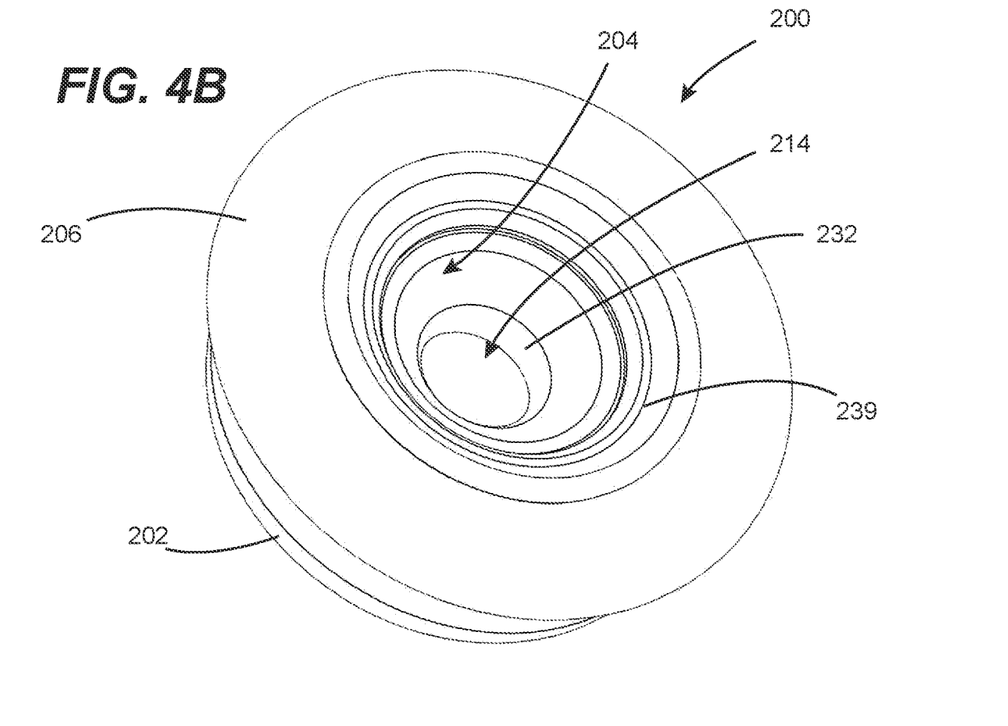
FIG. 4B is bottom perspective view of the trocar sealing device shown in FIG. 4A.
Figure 4C:
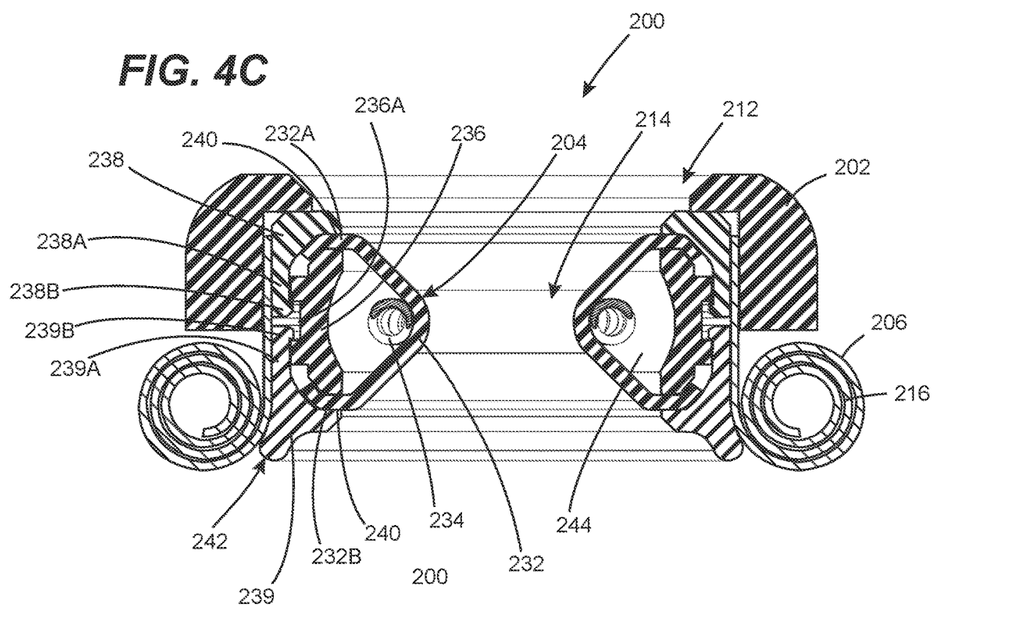
FIG. 4C is a cross-sectional view taken along the line 4C-4C in FIG. 4A.

FIGS. 4A-4C show a second embodiment of a trocar sealing device (sealing device 200) in accordance with the disclosures made herein. The sealing device 200 has an overall construction and functionality similar to that the sealing device 100 discussed above in reference to FIGS. 3A-3D. The differentiating aspects of the sealing device 200 of FIGS. 4A-4C with respect to the sealing device 100 of FIGS. 3A-3D will now be discussed without specific discussion of the similarity in the overall construction and functionality to that of the sealing device 100 discussed above in reference to FIGS. 3A-3D.

The sealing device 200 includes a support body 202, an extension member seal 204 and a securement body 206. The support body 202 can be attached to the extension member seal 204 and/or the securement body 206. The securement body 206 can be attached to the support body 202 and/or the extension member seal 204. In the same or similar manner as discussed above in reference to the sealing device 100 of FIGS. 3A-3D, the securement body 206 enables the sealing device 200 to be engaged with a seal housing of a trocar (e.g., the seal housing 54 of the trocar 50 of FIG. 2). For example, the securement body 206 can include an elongated skirt 116 or other form of trocar engaging element for enabling the sealing device 200 to be attached to a trocar.

The extension member seal 204, which can be used as a sealing device in standalone apparatuses and implements, comprises a sealing member 232, a compressive force member 234, an interior sealing member retainer 236, an upper exterior sealing member retainer 238 and a lower exterior sealing member retainer 239. The interior sealing member retainer 236 and the exterior sealing member retainers 238, 239 jointly form a retention body 242 having opposing retention structures that each retain one of the opposing end portions 232A, 232B of the sealing member 232. Engagement of the opposing end portions 232A, 232B of the sealing member 232 with the retention body 242 provides an interior space 244 between the sealing member 232 and the retention body 242. As shown, in one or more embodiments, the exterior sealing member retainers 238, 239 each include an annular shoulder 238A, 239A with a retention member 238B, 239B. The retention members 238B, 239B each engage a mating retention recess 236A of the interior sealing member retainer 236. The opposing end portions 232A, 232B of the sealing member 232 are each retained within a respective retention slot 240 formed between adjacent portions of the interior sealing member retainer 236 and the exterior sealing member retainers 238, 239. In this manner, each slot 240 serves as a spaced-apart sealing member retention portions of the retention body 242.

The compressive force member 234 is located within the interior space 244 between the sealing member 232 and the retention body 242 and extends partially (e.g., 350-degrees), exactly (e.g., 360-degrees), or more than fully (e.g., 380-degrees) around a central passage 214 of the sealing member 232 (i.e., around a longitudinal centerline reference axis of the central passage 214). For example, the compressive force member 234 can be a ring-shaped member. Examples of the ring-shaped member include, but are not limited to, a helically-round spring with attached and/or overlapping end portions, a polymeric O-ring, an elastomeric O-ring, a synthetic rubber O-ring, a rubber band, a c-spring (e.g., opposing ends spaced part) and the like. Additionally, it is disclosed herein that the interior space 244 between the sealing member 232 and the retention body 242 can be a fluidic material (e.g., a flowable material such as liquid, gaseous, gelatinous, etc). It is disclosed herein that the aforementioned compressive force members and the aforementioned flowable material provide common functionality (i.e., exertion of compressive force on the sealing member 232) and are both examples of a compressive force material in accordance with the disclosure made herein.

The sealing member 232 is positioned within a central passage of the compressive force member 234 prior to the opposing end portions 232A, 232B of the sealing member 232 being engaged with the retention body 242. It is disclosed herein that, in one or more embodiments, a ring-shaped member can be a unitary component of the sealing member (i.e., extruded or molded therein). The distance between the opposing end portions 232A, 232B of the sealing member 232 with the respective slot of the retention body 242 is such that the sealing member 232 is pulled at least tautly (or alternatively tightly) against the compressive force member 234. In this manner, the compressive force member 234 exerts a radial inward force on the sealing member 232 (i.e., the sealing member 232 maintains the compressive force member 234 is in a radially-expanded state from a static state, at rest state such that a compressive force is exerted on the sealing member 232 by the compressive force member 234).

The central passage 214 of the sealing member 232 is round (or approximately round) and has an inside diameter sized as a function of an outside diameter of an extension member of surgical instruments intended to be used with a trocar on which the sealing device 100 is mounted. As can be seen in FIG. 4C, engagement of the sealing member with the retention body (i.e., a free length of the sealing member 232 between the slots 240 of the retention body 242), engagement of the compressive force member 234 with the sealing body 232 and a thickness of the sealing member 232 jointly define a diameter of the central passage 214 of the extension member seal 204. As similarly discussed above in reference to FIGS. 3A-3D, the underlying objective of dimensional specification of the inside diameter of the central passage 212 of the sealing member 232 is to form secure engagement of the material of the sealing member 232 defining the central passage 212 around the extension member of the surgical instrument (i.e., being sealingly engaged) during the various modes of movement of the surgical instrument relative to the trocar—i.e., axial, pivotal and rotational movements. To this end, the sealing member 232 can be a sleeve (e.g., a thin-walled piece of flexible and/or conformable tubing (i.e., a tubular body)) made from a resilient material. For example, the sealing member 232 can be made from a material comprising or consisting essentially of an elastomer or synthetic rubber (e.g., a material comprising or consisting essentially of silicone).

As shown in FIG. 4C, the sealing member 232 has a centrally tapered shape (e.g., an hourglass shape). In combination with the compressive force member 234, this shape contributes to the sealing member 232 being able to expand around a variety of diameters while maintaining its stability and contributing minimal friction to the insertion of an elongated portion of a device (e.g., a surgical instrument). A medial portion of the sealing member 232 contributes an inwardly compressive radial force on an inserted elongation portion of a device and the opposing end portions 232A, 232B of the sealing member contribute an outward compressive force to the retention body 242 with which the sealing member is engaged. Additionally, open space around the medial portion of the sealing member 232 allows for a greater freedom of expansion and device tracking without imparting unacceptable insertion drag on the elongated portion of the device.

Advantageously, the extension member seal 204 provides for improved sealing of an extension member of an apparatus (e.g., a surgical instrument such as a laparoscope or other type of apparatus having an extension member). In particular, the extension member seal 204 provides for improved sealing of the extension member of apparatus that exhibits various modes of movement of the apparatus relative to a structure upon which the extension member seal 204 is mounted—i.e., lateral, axial, pivotal and rotational movements. Such sealing by the extension member seal 204 of an extension member of an apparatus that exhibits various modes of movement is referred to herein as multi-axis dynamic sealing. More specifically, multi-axis dynamic sealing refers to the construction and interaction of the sealing unit (e.g., a sealing member and a compressive force member thereof) providing a sealing interface that is capable of movement and/or conforming along a plurality of axes. It is disclosed herein that that such multi-axis dynamic sealing is not unnecessarily limited to being provided by any particular structure. For example, in addition to or alternatively to, multi-axis dynamic sealing can be provided through geometric of a single piece of material—e.g., a 3-dimensional structure such as an elastomeric sealing body having concentric wavy (e.g., sinusoidal waves in a cross-sectional view) rings extending around a central passage. The wavy rings provide available 3-dimensional material that enables movement of the central passage (e.g., lateral displacement) without causing stress/strain in the sealing body material resulting in unacceptable deformation of the central passage.

In one or more embodiments, the above-discussed axial alignment of a central passage of an extension member seal in accordance with the disclosure made herein (e.g., the extension member seal 104 or 204) with a working channel of a trocar (e.g., a commercially-available trocar) can be achieved by using an extension member to axially align the central passage of the extension member seal with the central passage of the trocar during engagement of the sealing device onto the seal housing of the trocar. A longitudinal axis of a central passage of the seal housing that extends colinearly with a longitudinal axis of a central passage of a cannula thereby jointly defining a longitudinal axis of the working channel. To perform such axial alignment, a distal end portion of the extension member of a surgical instrument or an extension member seal installer device (e.g., an extension member with handle attached to a proximate end portion thereof) can be inserted through the central passage of the extension member seal and the extension member then inserted into the working channel of the trocar until the extension member seal comes into contact with a top surface of the seal housing. The surgical instrument and the extension member seal installer device are examples of an alignment device having an extension member. In this regard, the elongated skirt is a seal housing engagement portion of the securement body that is selectively engageable with the seal housing and unrolling the elongated skirt is an embodiment of engaging a seal housing engagement portion of the securement body with the seal housing.

With the extension member seal in contact with the top surface of the seal housing, a skirt of the sealing device can be unrolled over one or more side surfaces of the seal housing and, optionally, over features protruding therefrom (e.g., as shown in FIG. 3D). The central passage of the extension member seal is now axially aligned with the working channel of the trocar, and the extension member can optionally be withdrawn from within the central passage of the extension member seal and the working channel of the trocar.

Aligning the longitudinal axis of the central passage of the extension member seal with the longitudinal axis of the working channel can be performed in conjunction with contacting the sealing device with the top surface of the seal housing. This can include inserting the distal end portion of the extension member through the central passage of the extension member seal and inserting the distal end portion of the extension member into the working channel. In one technique, prior to unrolling the skirt, the distal end portion of the extension member can be inserted through the central passage of the extension member seal and the distal end portion of the extension member can be inserted into the working channel. For example, inserting the distal end portion of the extension member through the central passage of the extension member seal can be performed after contacting the sealing device with the top surface of the seal housing and prior to inserting the distal end portion of the extension member into the working channel.

In one or more embodiments, the extension member seal installer device can be an obturator used for placing the trocar through the abdominal wall (or other body cavity wall) of a patient. In one or more other embodiments, the extension member seal installer device can be a laparoscope used during a surgical procedure after placing the trocar through the abdominal wall (or other body cavity wall) of the patient. In preferred embodiments, a sealing device in accordance with the disclosures herein is engaged with the trocar after its placement in the patient.

Figure 5:
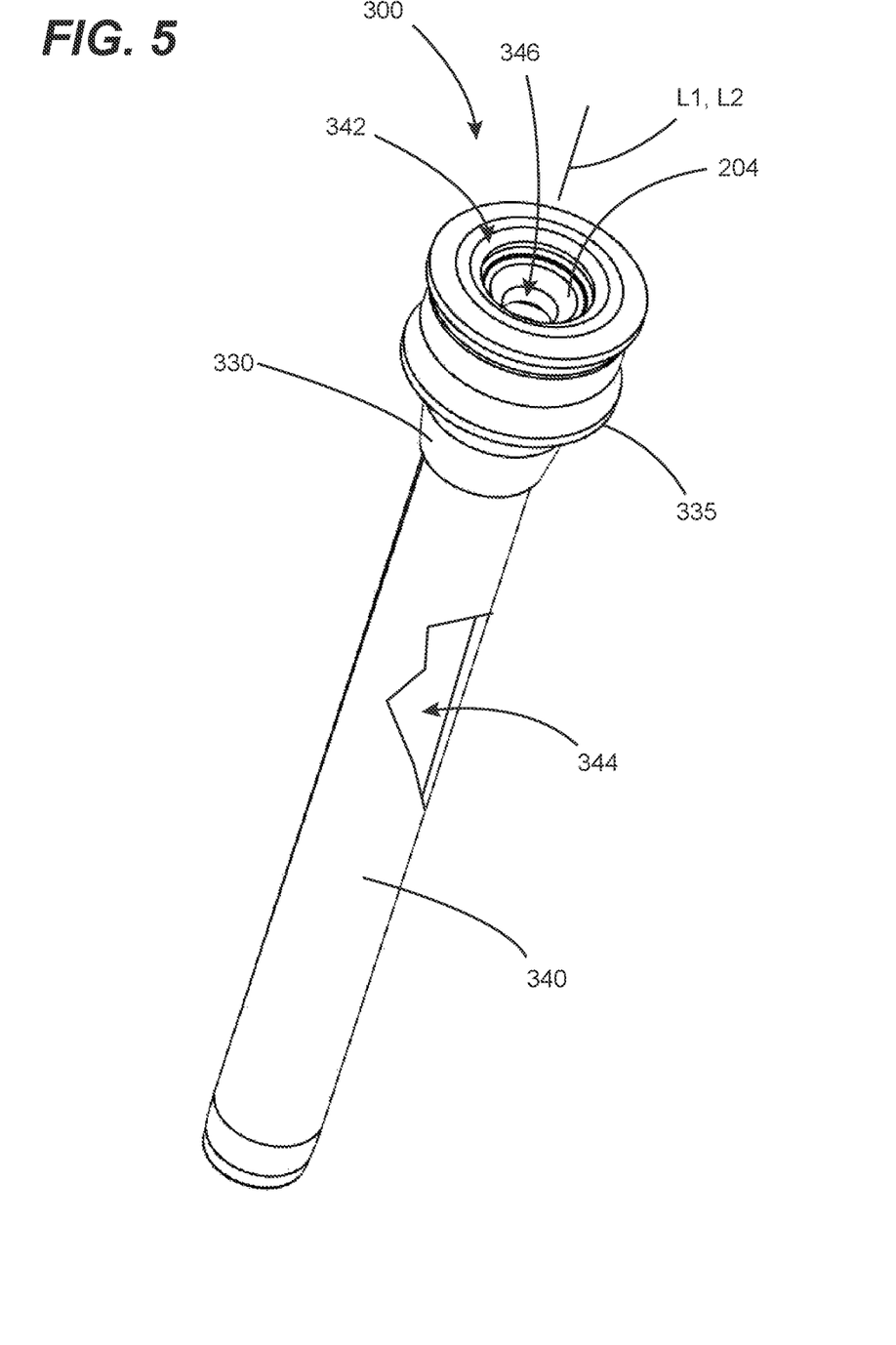
FIG. 5 is a perspective view showing an embodiment of a trocar in accordance with the disclosures made herein.

Referring now to FIG. 5, a sealing apparatus 300 configured in accordance with the disclosures made herein is shown. As shown, the sealing apparatus 300 is a trocar used in surgical procedures. However, in other embodiments, the sealing apparatus 300 can be useful in other applications and industries non-related to surgical procedures. The sealing apparatus 300 include a trocar body 330 (i.e., a support body) and the extension member seal 204 (shown in FIGS. 4A-4C) mounted on a seal housing 335 of the trocar body 330. A cannula 340 extends from the seal housing 306. A longitudinal axis L1 of the seal housing 335 is axially aligned with a longitudinal axis L2 of the cannula 340 such that the seal housing 335 and the cannula 340 have longitudinal axes that are colinear. A central passage 342 of the seal housing 335 defines the longitudinal axis L1 thereof and a central passage 344 of the cannula 340 defines the longitudinal axis L2 thereof. Jointly, the central passage of the seal housing 335 and the central passage of the cannula 340 define a working channel 346 of the trocar 300. In this regard, incorporation of the extension member seal 204 of FIGS. 4A-4C results in the trocar advantageously exhibiting multi-axis dynamic sealing in accordance the disclosures made herein.

EXAMPLE

Assessment Of Reduction in Insufflation Gas Leakage Through Trocar-Laparoscope Interface by Trocar Sealing Device Materials

TABLE 1

| MATERIALS |
| --- |
| Trocar from Applied Medical Resources Corporation; Kii Fios; Model No. CTF03; 5 × 100 mm |
| Laparoscope from Stryker; Precision Model no. 0502-503-010; 5 mm diameter 0-degree end face |
| Latex elastic O-ring; Sectioned from piece of thin-walled tubing to provide a rectangular cross-section O-ring (4.7625 ID, 6.35 mm OD, 4.45 mm Height); 40 A Durometer |
| Silicone elastic tubing (10.83 mm ID, 13.87 OD, 47.91 mm Length); Medium Soft Durometer (about 40 A) |
| Commercially-available sewing thread |
| Rigid PVC pipe |
| Air compressor |
| Air pressure regulator |
| Mass flow meter |
| Tape measure |
| Air flow conduit |
| Data logger |
| Laptop with data logger interface |

Trocar Sealing Device Construction

The silicone elastic tubing was extended through the central opening of the latex elastic O-ring. A portion of the tubing was then partially folded over the O-ring, and sewn to constrain the O-ring within the folded-over portion of the tubing to thereby produce a trocar sealing device. The folded-over portion of the tubing was nominally 12.12 mm long such that the remaining portion of the tubing formed a 35.97 mm long skirt extending below the O-ring.

Test Configurations

TABLE 2

| TEST CONFIGURATIONS | |
| --- | --- |
| Configuration | Set-Up |
| 1 | As-manufactured trocar; No trocar sealing device engaged with head of trocar; 5 mm shaft of laparoscope extending through central passage of trocar |

TABLE 2-continued

TEST CONFIGURATIONS

| Configuration | Set-Up |
|---|---|
| 2 | As-manufactured trocar; Trocar sealing device engaged with head of trocar; 5 mm shaft of laparoscope engaged through central passage of trocar sealing device and central passage of trocar |
| 3 | Modified trocar (with plastic head adapter and internal valve unit removed to provide trocar without insufflation gas containment capability); Trocar sealing device engaged with head of trocar; 5 mm shaft of laparoscope engaged through central passage of trocar sealing device and central passage of modified trocar |

Test Equipment Set-Up

The test equipment set-up included the following steps:

1. Attach a first end portion of a length of PVC pipe to in-vivo end of trocar in a sealed manner to create an insufflation chamber.

2. Using the air flow conduit, connect the air compressor to air pressure regulator, the air pressure regulator to the mass flow meter, the mass flow meter to the insufflation chamber at the second end portion of the length of PVC pipe.

3. Turn on the mass flow meter, data logger, laptop and air compressor.

4. Record the initial mass flow meter pressure reading for ambient room pressure.

5. With the air pressure regulator valve closed, adjust the mass flow meter until the pressure is +15 mmHg greater than the ambient room pressure reading.

6. Lay the tape measure along the length of the insufflation chamber with at least 6" of the tape measure extended past the end of the insufflation chamber that includes the laparoscope port of the trocar.

7. For test configuration 1, insert the shaft of the laparoscope into the port of the trocar until only 3 inches of the laparoscope shaft remains exposed outside of the insufflation chamber.

8. For test configurations 2 and 3, place the trocar sealing device over the port end of the trocar and then insert the shaft of the laparoscope through the central passage of the trocar sealing device and into the port of the trocar until only 3 inches of the laparoscope shaft remains exposed outside of the insufflation chamber.

Test Procedures and Results

Procedure 1: Static (motionless) use case testing. This is a "uncompromised valve scenario" use case. Although it does occur, the likelihood during a case of laparoscopic instruments (e.g. a laparoscope) of this scenario is not common. This is a best-case scenario because there is no leak-compromising interaction between instrument-trocar valve interface.

The laparoscope was left to rest inside the insufflation chamber for 30 seconds, while measuring a gas leakage rate of air passing out of the insufflation chamber at the interface between the shaft of the laparoscope and the central passage of the trocar sealing device. Three (3) trials of this test procedures were performed for each of the trocar sealing device constructions and the average of these three trials was computed and recorded.

Procedure 1 Results:

TABLE 3

Procedure 1 Results

| Configuration | Average Leak Rate (mL/s) | Average Total Leakage over~30 second Procedure (mL) | Estimated Total Leakage Volume of 1 hour of surgery through 1 trocar port (mL) |
|---|---|---|---|
| 1 | 0.062968 | 1.826029 | 219.123 |
| 2 | 0.058975 | 1.768665 | 212.239 (−3.1%) |
| 3 | 0.059695 | 1.72989 | 2.07.586 (−5.3%) |

The results for this test procedure show relatively comparable performance between the configurations during this static use case testing. Although relatively comparable, it is worth noting that the configurations with the trocar sealing device outperformed the commercially-available trocar.

Procedure 2: Dynamic (motion) use case testing. This is a "motion compromised valve scenario" use case for laparoscopic surgeries because such surgeries require the near-constant movement of instruments throughout the entirety of surgery. Even the most minor movements may create motion which may still compromise insufflation leakage scenarios through interaction at the instrument-trocar valve interface.

The laparoscope was left to rest inside the Trocar setup Configuration with roughly 3 inches of the scope instrument left protruding, and then was slowly retracted 3 inches and slowly re-inserted 3 inches back to its original resting state. The rate of movement was roughly 1 in/second. Three (3) trials of this test procedures were performed for each of the trocar sealing device constructions and the average of these three trials was computed and recorded.

Procedure 2 Results:

TABLE 4

Procedure 2 Results

| Configuration | Average Leak Rate (mL/s) | Average Total Leakage over~45 second Procedure (mL) | Estimated Total Leakage Volume of 1 hour of surgery through 1 trocar port (mL) |
|---|---|---|---|
| 1 | 0.184493 | 8.149929 | 651.994 |
| 2 | 0.135028 | 6.019311 | 481.544 (−26%) |
| 3 | 0.136944 | 5.80192 | 464.153 (−29%) |

The results for this test procedure show significantly greater performance for the test configurations including the trocar sealing device. Notably, the trocar sealing device alone can provide exceptional insufflation gas leakage mitigation.

CONCLUSIONS

The above example illustrate that insufflation gas leakage can be reduced (i.e., mitigated) by implementation of trocar sealing devices in accordance with the disclosures made herein during surgical procedures. In particular, the test results for Procedure 2 show that use of such a trocar sealing device notably reduces insufflation leakage. Furthermore, results of Configurations 2 and 3 even further illustrate that the sealing valve structure already found in some commerciality-available trocars is rendered moot with the inclusion of trocar sealing devices configured in accordance with embodiments of the disclosures made herein. Finally, such reductions in insufflation gas leakage provided for by trocar sealing devices in accordance with the disclosures made herein can be critically valuable in the era of COVID-19. During in vivo exposure of the insufflation gas in a patient suffering from COVID-19, the insufflation gas can become contaminated with the virus (i.e., Coronavirus) that causes COVID-19. Accordingly, leakage of such contaminated insufflation gas can expose the operating room (OR) and personnel therein to Coronavirus. Use of a trocar sealing in accordance with the disclosures made herein can beneficially reduce this exposure.

Although the invention has been described with reference to several exemplary embodiments, it is understood that the words that have been used are words of description and illustration, rather than words of limitation. Changes may be made within the purview of the appended claims, as presently stated and as amended, without departing from the scope and spirit of the invention in all its aspects. Although the invention has been described with reference to particular means, materials and embodiments, the invention is not intended to be limited to the particulars disclosed; rather, the invention extends to all functionally equivalent technologies, structures, methods and uses such as are within the scope of the appended claims.

What is claimed is:

1. A sealing device for a trocar configured for use with a surgical instrument, comprising:
   an extension member seal having a central passage with a diameter enabling an extension member of the surgical instrument to be sealingly engaged with the extension member seal; and
   a securement body attached to the extension member seal, wherein the securement body includes an elongated skirt in a rolled configuration and wherein the elongated skirt is adapted for being unrolled into secure engagement with one or more side surfaces of a seal housing of the trocar.

2. The sealing device of claim 1 wherein:
   the elongated skirt extends entirely around the extension member seal; and
   the elongated skirt is concentric with the central passage of the extension member seal.

3. The sealing device of claim 1 wherein:
   the elongated skirt is a sleeve; and
   an end portion of the sleeve is attached to the extension member seal.

4. The sealing device of claim 3 wherein the sleeve is a piece of tubing.

5. The sealing device of claim 3 wherein:
   the sleeve extends entirely around the extension member seal; and
   the sleeve is concentric with the central passage of the extension member seal.

6. The sealing device of claim 5 wherein the elongated skirt being adapted for being unrolled includes the elongated skirt being made from a conformable, resilient material.

7. The sealing device of claim 6 wherein the conformable, resilient material is one of a material comprising silicone and a material consisting essentially of silicone.

8. The sealing device of claim 1 wherein the elongated skirt being adapted for being unrolled includes the elongated skirt being made from a conformable, resilient material.

9. A sealing device for a trocar configured for use with a surgical instrument, comprising:
   an extension member seal having a central passage with a diameter enabling an extension member of the surgical instrument to be sealingly engaged with the extension member seal;
   a securement body attached to the extension member seal, wherein the securement body includes an elongated skirt in a rolled configuration and wherein the elongated skirt is adapted for being unrolled into secure engagement with one or more side surfaces of a seal housing of the trocar; and
   a support body attached to the extension member seal, wherein the support body includes a central passage through which the central passage of the extension member seal is accessible, wherein the support body is attached to an upper portion of the extension member seal and the elongated skirt is positioned adjacent to a lower portion of the extension member seal.

10. The sealing device of claim 9 wherein:
    the elongated skirt extends entirely around the extension member seal; and
    the elongated skirt is concentric with the central passage of the extension member seal.

11. The sealing device of claim 9 wherein the elongated skirt extends entirely around the extension member seal.

12. The sealing device of claim 9 wherein the elongated skirt being adapted for being unrolled includes the elongated skirt being made from a conformable, resilient material.

13. A sealing device for a trocar configured for use with a surgical instrument, comprising:
    an extension member seal having a central passage with a diameter enabling an extension member of the surgical instrument to be sealingly engaged with the extension member seal;
    a securement body attached to the extension member seal, wherein the securement body includes an elongated skirt in a rolled configuration, wherein the elongated skirt is adapted for being unrolled into secure engagement with one or more side surfaces of a seal housing of the trocar and wherein the elongated skirt extends entirely around the extension member seal; and
    a support body attached to the extension member seal, wherein the support body includes a central passage through which the central passage of the extension member seal is accessible, wherein the support body is attached to an upper portion of the extension member seal and the elongated skirt is positioned adjacent to a lower portion of the extension member seal.

14. The sealing device of claim 13 wherein:
    the elongated skirt is a sleeve; and
    an end portion of the sleeve is attached to the extension member seal.

15. The sealing device of claim 14 wherein the sleeve is a piece of tubing.

16. The sealing device of claim 13 wherein the elongated skirt is generally concentric with the central passage of the extension member seal.

17. The sealing device of claim 16 wherein:
    the elongated skirt being adapted for being unrolled includes the elongated skirt being made from a conformable, resilient material; and
    the conformable, resilient material is one of a material comprising silicone and a material consisting essentially of silicone.

18. The sealing device of claim 16 wherein the elongated skirt being adapted for being unrolled includes the elongated skirt being made from a conformable, resilient material.

19. The sealing device of claim 13 wherein the elongated skirt is made from one of a material comprising silicone and a material consisting essentially of silicone.

20. The sealing device of claim 13 wherein the elongated skirt being adapted for being unrolled includes the elongated skirt being made from a conformable, resilient material.

\* \* \* \* \*